(12) United States Patent
Park

(10) Patent No.: US 9,872,708 B2
(45) Date of Patent: Jan. 23, 2018

(54) MEDICAL DEVICE FOR PECTUS EXCAVATUM DEFORMITY CORRECTION SURGERY

(71) Applicant: Hyung Joo Park, Seoul (KR)

(72) Inventor: Hyung Joo Park, Seoul (KR)

(*) Notice: Subject to any disclaimer, the term of this patent is extended or adjusted under 35 U.S.C. 154(b) by 0 days.

(21) Appl. No.: 15/439,931

(22) Filed: Feb. 22, 2017

(65) Prior Publication Data

US 2017/0156759 A1 Jun. 8, 2017

Related U.S. Application Data

(63) Continuation of application No. PCT/KR2016/008668, filed on Aug. 5, 2016.

(30) Foreign Application Priority Data

Aug. 5, 2015 (KR) .................. 10-2015-0110646

(51) Int. Cl.
*A61B 17/88* (2006.01)
*A61B 17/68* (2006.01)

(52) U.S. Cl.
CPC .......... *A61B 17/68* (2013.01); *A61B 17/8866* (2013.01); *A61B 17/8869* (2013.01); *A61B 2017/681* (2013.01)

(58) Field of Classification Search
CPC ................. A61B 2017/681; A61B 17/8076
See application file for complete search history.

(56) References Cited

U.S. PATENT DOCUMENTS 4,327,715 A * 5/1982 Corvisier ........... A61B 17/8076
606/71
6,024,759 A * 2/2000 Nuss ...................... A61B 17/68
606/237

(Continued)

FOREIGN PATENT DOCUMENTS

KR    10-2004-0028009 A    4/2004
KR       10-0828111 B1    5/2008

(Continued)

OTHER PUBLICATIONS

International Search Report dated Dec. 13, 2016 in application No. PCT/KR2016/008668.

(Continued)

*Primary Examiner* — David Bates
(74) *Attorney, Agent, or Firm* — Maschoff Brennan

(57) ABSTRACT

A pectus excavatum correction apparatus includes two pectus bars each made of a stick plate. Each bracket of the apparatus has a plate shape with a length-direction bent part. The first side of the bent part is hooked onto an upper or lower part of a rib and a second side of the bent part faces an outer surface of the pectus bar. Each of a first and second bridge has through-holes provided in two length-direction ends of the bridge. Each coupling unit includes a supporting part provided between the rib and the pectus bar, a slide protruding from an outer surface of the supporting part, and a second coupling part coupled to the first coupling part to press and fix the pectus bar, the bracket, and the bridge. The second distance is greater or less than the first distance within a preset range.

5 Claims, 6 Drawing Sheets

(56) References Cited

U.S. PATENT DOCUMENTS

| | | | |
|---|---|---|---|
| 6,669,697 B1* | 12/2003 | Pisharodi | A61B 17/7007 606/250 |
| 2006/0058786 A1 | 3/2006 | Kim et al. | |
| 2010/0100142 A1* | 4/2010 | Park | A61B 17/8872 606/86 R |
| 2010/0256691 A1* | 10/2010 | Park | A61B 17/8076 606/330 |
| 2010/0331892 A1* | 12/2010 | Fell | A61B 17/8076 606/286 |
| 2011/0251540 A1* | 10/2011 | Notrica | A61F 5/058 602/19 |
| 2012/0178069 A1* | 7/2012 | McKenzie | G09B 23/28 434/262 |
| 2012/0296440 A1* | 11/2012 | Choux | A61B 17/68 623/23.52 |
| 2014/0135853 A1* | 5/2014 | Reisberg | A61B 17/8076 606/324 |
| 2014/0163691 A1* | 6/2014 | Dartevelle | A61B 17/8076 623/23.53 |
| 2015/0134009 A1* | 5/2015 | Licht | A61B 17/8076 606/281 |

FOREIGN PATENT DOCUMENTS

| | | |
|---|---|---|
| KR | 10-1037957 B1 | 5/2011 |
| KR | 10-2013-0045007 A | 5/2013 |

OTHER PUBLICATIONS

Written Opinion dated Dec. 13, 2016 in application No. PCT/KR2016/008668.

* cited by examiner

MEDICAL DEVICE FOR PECTUS EXCAVATUM DEFORMITY CORRECTION SURGERY

CROSS-REFERENCE TO RELATED APPLICATIONS

This application is a continuation of international application no. PCT/KR2016/008668, filed on Aug. 5, 2016, which claims priority to Korean application no. 10-2015-0110646, filed Aug. 5, 2015. The foregoing applications are incorporated herein by reference.

TECHNICAL FIELD

The present invention relates to a medical apparatus for correcting pectus excavatum and, more particularly, to a medical apparatus for correcting pectus excavatum by preventing displacement of a pectus bar from a correction range thereof and thus continuously supporting inner sides of the sternum and rib cartilages until correction.

BACKGROUND ART

Chest wall deformities are generally divided into pectus excavatum, also called funnel chest, and pectus carinatum, also called pigeon chest.

As illustrated in FIG. 1, the rib cage includes ribs 10, a sternum 12, rib cartilages 14, and thoracic vertebrae 16, which are connected to each other.

In the rib cage, pectus excavatum and pectus carinatum do not refer to deformities in the ribs 10 but refer to deformities in the rib cartilages 14 interconnecting the ribs 10 and the sternum 12 positioned at the center of the chest.

It is reported that such deformities are not severe at birth but develop with age.

Particularly, in the case of pectus excavatum, a sunken chest wall presses the heart or the lungs and can cause functional disorders in the pressed part.

The Ravitch procedure and the Nuss procedure are known surgical treatments for pectus excavatum.

The Ravitch procedure involves making a large incision in the front chest and completely removing an abnormal rib cartilage through the incision. After surgery, the chest wall may be weakened, may lose soft motion functionality thereof due to adhesion, and may have a large scar thereon.

The Nuss procedure was invented by Dr. Donald Nuss (USA) in 1997 and is a procedure capable of replacing the Ravitch procedure to treat pectus excavatum.

In the Nuss procedure, for example, when a part of the chest wall indicated by hatched lines H in FIG. 2a is sunken, incisions of about 1 to 2 cm are made in the armpits, and a curved pectus bar 18 is inserted through the incisions as illustrated in FIGS. 2a and 2b.

Then, the curved pectus bar 18 is flipped in a direction indicated by an arrow A in FIGS. 2a and 2b, to push the sunken sternum 12 and the rib cartilage 14 outward as illustrated in FIG. 2c.

Subsequently, two ends of the pectus bar 18 are supported by the ribs 10 corresponding thereto until the chest is corrected to a normal chest wall shape.

As described above, compared to the Ravitch procedure, since surgical scars of only 1 to 2 cm are created at two sides of the chest and the chest is corrected to a normal chest wall shape without resecting the rib cartilage 14, the Nuss procedure may not only constantly maintain flexibility and resilience of the chest but also have a short operation time and a small amount of blood loss during operation.

In the Nuss procedure, the pectus bar 18 should be stably supported against restoring forces of the sternum and the rib cartilage 14, which tend to return to original states thereof before correction, until the sternum 12 and the rib cartilage 14 are corrected.

Detailed descriptions are now given of a process of correcting the sternum 12 and the rib cartilage 14 and of correlations between the process and the pectus bar 18.

Initially, immediately after correction from FIG. 2b to FIG. 2c, the sternum 12 and the rib cartilage 14 provide restoring forces to the pectus bar 18 to return to the deformed states thereof. The restoring forces are initially strong but are gradually reduced until correction is completed.

At an early stage of the above-described correction process, a surgeon inserts the pectus bar 18, which is designed to have a correction range and shape appropriate for a patient, to move the sternum 12 and the rib cartilage 14 to correction positions thereof against the strong restoring forces of the sternum 12 and the rib cartilage 14, and the two ends of the pectus bar 18 are fixed to and supported by the ribs 10 corresponding thereto to maintain the corrected state.

That is, the pectus bar 18 is provided at a position where the pectus bar 18 is flipped from FIG. 2b to FIG. 2c depending on judgment of the surgeon and, at the same time, supported by the ribs 10 against the restoring forces depending on strength of the surgeon.

The pectus bar 18 should continuously have an elastic force against the restoring forces of the sternum 12 and the rib cartilage 14.

The pectus bar 18 requires elasticity not only to respond to the restoring forces of the sternum 12 and the rib cartilage 14, but also to flexibly respond to cardiopulmonary exercise of the patient and physical forces applied from outside, together with the ribs 10.

Accordingly, at the early stage of correction, as illustrated in FIG. 2c, due to the strong restoring forces of the sternum 12 and the rib cartilage 14 in a direction indicated by an arrow B, a length-direction central part of the pectus bar 18 is slightly straightened compared to a designed shape thereof as indicated by an arrow B' and, at the same time, two length-direction ends of the pectus bar 18 are slightly straightened away from each other as indicated by an arrow B".

Then, for example, as illustrated in FIG. 2d, the pectus bar 18 is elastically transformed from a dashed line shape indicating the early stage of correction, to a solid line shape indicating a designed correction position.

Such transformation differs based on sizes and directions of the restoring forces of the sternum 12 and the rib cartilage 14, and a strength supported by the ribs 10.

That is, the pectus bar 18 is configured to flexibly respond to the restoring forces of the sternum and the rib cartilage 14 from the early stage of correction till the last stage of correction, and the two length-direction ends of the pectus bar 18 are variably fixed in length directions of the ribs 10 to respond to the restoring forces of the sternum 12 and the rib cartilage 14 and the elastic transformation of the pectus bar 18 based on the restoring forces.

Specifically, the position of the pectus bar 18 and, more particularly, the positions of the two ends thereof are not maintained but have clearance (tolerance) ranges in forward, backward, leftward, and rightward directions to respond to motion of the sternum 12, the rib cartilage 14, and the ribs 10 based on correction, and elastic restoration and transformation of the pectus bar 18.

The ribs 10, to which the pectus bar 18 is fixed, move from original curved positions thereof to positions indicated by the arrow B in FIG. 2c, and then slightly and continuously move during correction.

The restoring forces of the sternum 12 and the rib cartilage 14 are applied to the pectus bar 18 not only in forward, backward, leftward, and rightward directions based on the center of the pectus bar 18 but also in upward and downward directions based on the two ends of the pectus bar 18 supported by the ribs 10 as illustrated in FIG. 3.

Displacement of the pectus bar 18 due to the above-described restoring forces of the sternum 12 and the rib cartilage 14 may not only cause correction errors but also press and damage organs of a patient. A surgeon should pay close attention to avoid such problems.

DISCLOSURE

Technical Problem

Therefore, the present invention has been made in view of the above problems, and it is one object of the present invention to provide a medical apparatus for correcting pectus excavatum by responding to variations in restoring forces of the sternum and rib cartilages during correction and transformation including displacement of a pectus bar in forward, backward, leftward, and rightward directions based on the variations, and preventing displacement of a central part of the pectus bar in an upward or downward direction.

The above and other objects can be accomplished by the present invention described below.

Technical Solution

In accordance with one aspect of the present invention, provided is a pectus excavatum correction apparatus including two pectus bars each made of a stick plate having a width, thickness, length, curved shape, rigidity, and elastic restoring force designed to correspond to a predetermined treatment site of a patient, each including first long holes in length-direction ends thereof, and spaced apart from each other in a vertical direction of the patient; brackets each having a plate shape having a length-direction bent part, wherein a first side of the bent part is hooked onto an upper or lower part of a rib, a second side of the bent part crosses and faces an outer surface of the pectus bar, and a second long hole is provided in at least the second side of the bent part along a length direction of the bracket; a first bridge having through-holes provided in two length-direction ends of the first bridge and spaced apart from each other by a preset first distance to correspond to end-direction positions of the pectus bars within the upper and lower first long holes; a second bridge for configuring a set together with the first bridge and having through-holes provided in two length-direction ends of the second bridge and spaced apart from each other by a preset second distance to correspond to center-direction positions of the pectus bars within the upper and lower first long holes; and coupling units each including a supporting part provided between the rib and the pectus bar, a slide protruding from an outer surface of the supporting part and inserted to be slidable along the first long hole, a first coupling part provided at a center of an outer surface of the slide, and a second coupling part coupled to the first coupling part to press and fix the pectus bar, the bracket, and the bridge provided on a coupling path between the first and second coupling parts through an overlapping part of the first and second long holes and the through-hole, wherein the second distance is greater or less than the first distance within a preset range.

The second bridge may be fixed using the coupling units without using the brackets to correspond to the first long holes of the pectus bars.

A height of the slide protruding from the outer surface of the supporting part may be greater than the thickness of the pectus bar, the bracket and the bridge may be fixed to each other by receiving support of the outer surface of the slide and coupling the first coupling part to the second coupling part, and the pectus bar may be guided by the slide to be slidable along a length direction of the first long hole.

The first coupling part may include a bolt integrally protruding from the outer surface of the supporting part, the supporting part may include a plug extending and protruding therefrom to cross the pectus bar and to be inserted into the second long hole, and a first rough surface provided around the first coupling part on the outer surface of the supporting part, and the slide may include a hole for penetrating the bolt therethrough, and second rough surfaces provided around the hole on inner and outer surfaces of the slide to correspond to the first rough surface.

In accordance with another aspect of the present invention, provided is a pectus excavatum correction apparatus including pectus bars each having a width, thickness, length, curved shape, rigidity, and elastic restoring force designed to correspond to a predetermined treatment site of a patient, and each including first long holes in length-direction ends thereof along a center line of the width; brackets each having a plate shape having a length-direction bent part, wherein a first side of the bent part is hooked onto an upper or lower part of a rib, a second side of the bent part crosses and faces an outer surface of the pectus bar, and a second long hole is provided in at least the second side of the bent part along a length direction of the bracket; and coupling units each including a supporting part having a plate shape provided between the rib and the pectus bar and including a bolt integrally protruding from a center of an outer surface of the supporting part, a plug extending therefrom to be inserted into the second long hole, and a first rough surface provided around the bolt on the outer surface of the supporting part, a slide inserted to be slidable along the first long hole and including a hole for penetrating the bolt therethrough, and second rough surfaces provided around the hole on inner and outer surfaces of the slide to correspond to the first rough surface, and a nut coupled to the bolt protruding through an overlapping part of the first and second long holes and the through-hole to press and fix the bracket provided between the bolt and the nut.

Advantageous Effects

According to the present invention, since two pectus bars are separately provided at upper and lower parts of the sternum, rigidity and elasticity required to correct pectus excavatum may be divided and a larger area may be supported compared to one pectus bar, thereby achieving stability. Furthermore, the upper and lower pectus bars may disperse restoring forces of the sternum and rib cartilages and may complementarily prevent displacement thereof.

In addition, coupling units supporting the pectus bars may prevent elastic transformation and displacement of the pectus bars corresponding to restoring forces of the sternum and rib cartilages toward original states thereof before correction and external physical forces pressing the chest, thereby achieving stable correction.

In addition, a third bridge according to a modified embodiment may not only support the distance between the upper and lower pectus bars but also complementarily prevent displacement of the pectus bars.

BEST MODE

Figure 1:
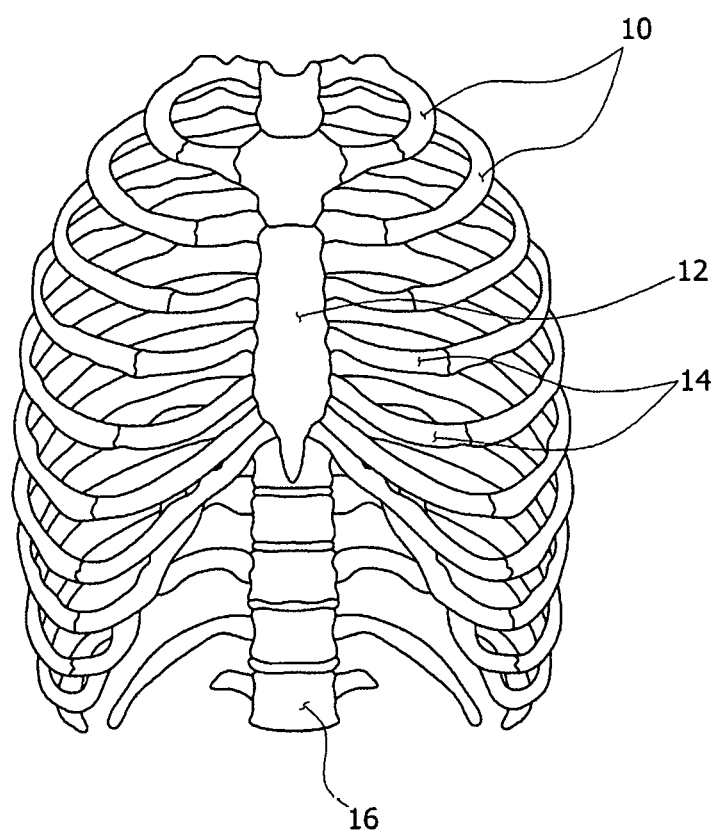
FIG. 1 is a front view of the rib cage.
Figure 2A:
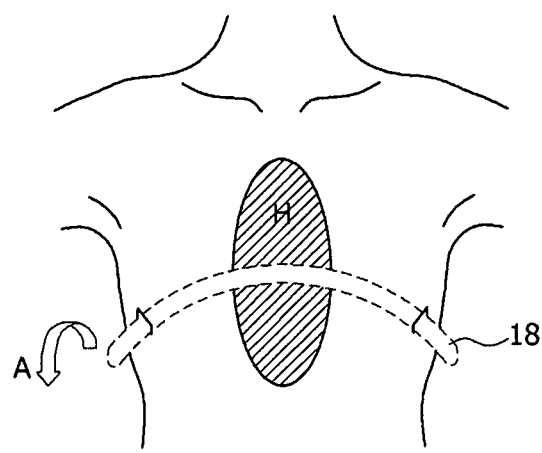
FIGS. 2a to 2d are schematic diagrams for describing a process of correcting pectus excavatum based on the Nuss procedure.
Figure 2B:
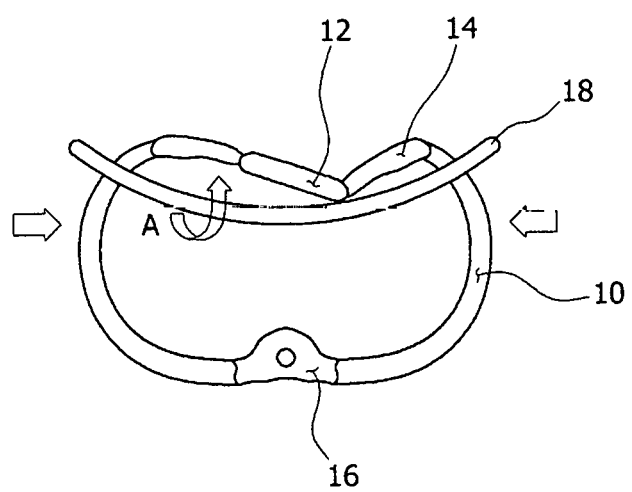
Figure 2C:
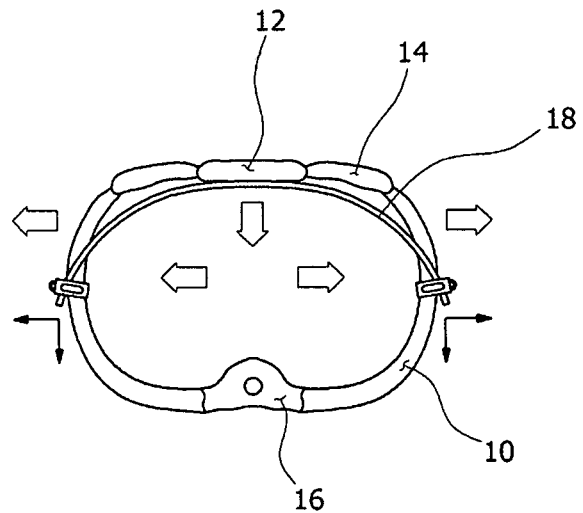
Figure 2D:
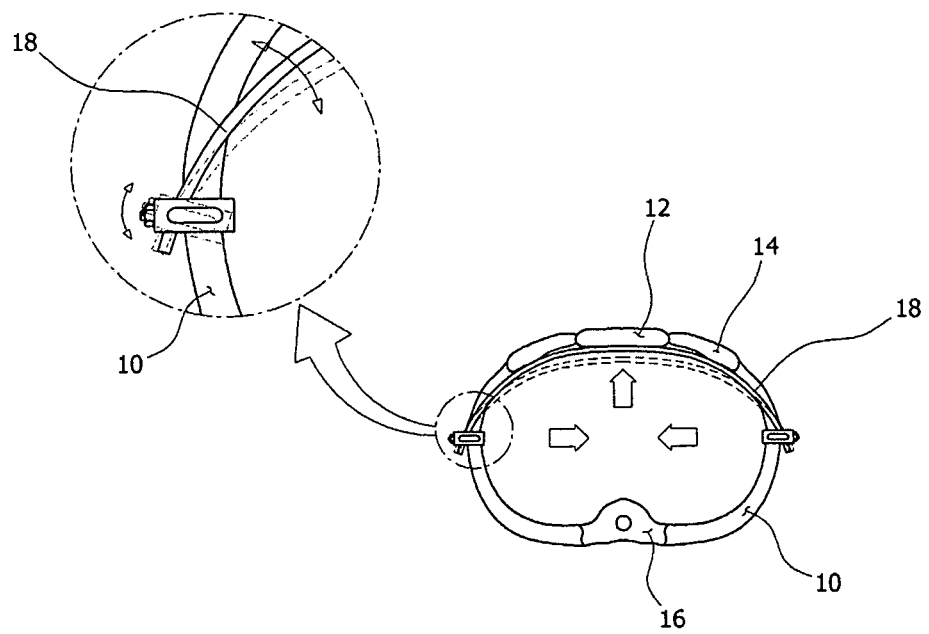

In the following description, "upper" or "upper part" indicates an upward direction toward the head of a patient who stands upright, or a part in the upward direction, and "lower" or "lower part" indicates a direction opposite to the upward direction, i.e., a downward direction toward the legs of the patient, or a part in the downward direction.

"Inner side" indicates an inner part surrounded by the thoracic vertebrae, ribs, rib cartilages, and sternum, or a direction thereof, and "outer side" indicates an outer part opposite to the inner part, or a direction thereof.

"Front" or "front part" indicates a forward direction of the patient who stands upright, or a part in the forward direction, and "rear" or "rear part" indicates a backward direction of the patient, or a part in the backward direction.

Hereinafter, the present invention will be described in detail by explaining embodiments of the invention with reference to the attached drawings. Like reference numerals in the drawings denote like elements, and elements described above in the background art will not be repeatedly described below.

Figure 3:
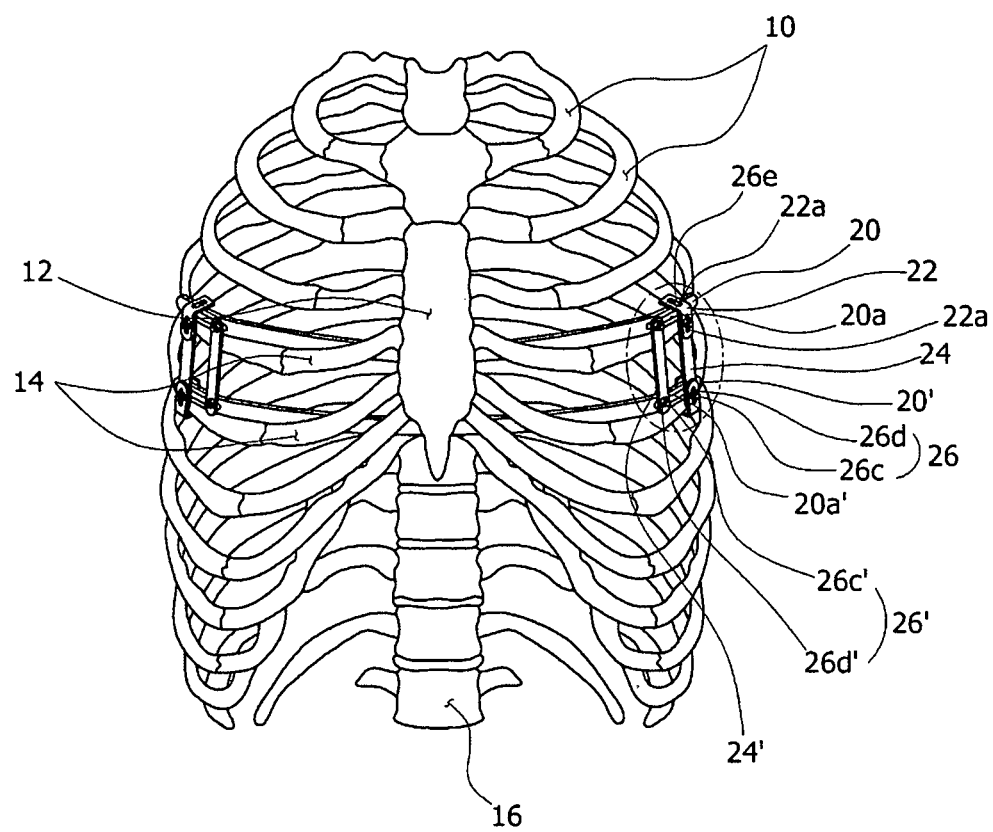
FIG. 3 is a perspective view for describing a process of correcting pectus excavatum, according to an embodiment of the present invention.

As illustrated in FIG. 3, a medical apparatus for correcting pectus excavatum, according to an embodiment of the present invention, includes two pectus bars 20 and 20', brackets 22 hooked onto upper and lower parts of ribs 10 to be coupled to the pectus bars 20 and 20', bridges 24 and 24' for interconnecting the two pectus bars 20 and 20', and coupling units 26 and 26' for fixing the pectus bars 20 and 20', the brackets 22, and the bridges 24 and 24' to each other.

Among the above-described elements of the present invention, the pectus bars 20 and 20' have curved shapes having a width W1, a thickness T1, a length, and a length direction and corresponding to predetermined treatment sites of a patient, and are designed in consideration of elastic restoring forces based on the curved shapes.

Herein, the elastic restoring forces of the pectus bars 20 and 20' are designed based on accumulated data about the severity of deformity of the sternum 12 and the rib cartilages 14 at the treatment sites, and restoring forces of the sternum 12 and the rib cartilages 14, which tend to return to original shapes thereof before correction.

First long holes 20a and 20a' are provided in two length-direction ends of the pectus bars 20 and 20' along a center line of the width W1.

Among the elements of the present invention, each of the brackets 22 has a width W2, a length, and a thickness T2, and a plate shape having a length-direction bent part. A first side of the bent part is hooked onto an upper or lower part of the rib 10, and a second side of the bent part crosses and closely faces the pectus bar 20 or 20'.

A second long hole 22a is provided in at least the second side of the bent part of the bracket 22 along a length direction of the bracket 22.

Figure 4:
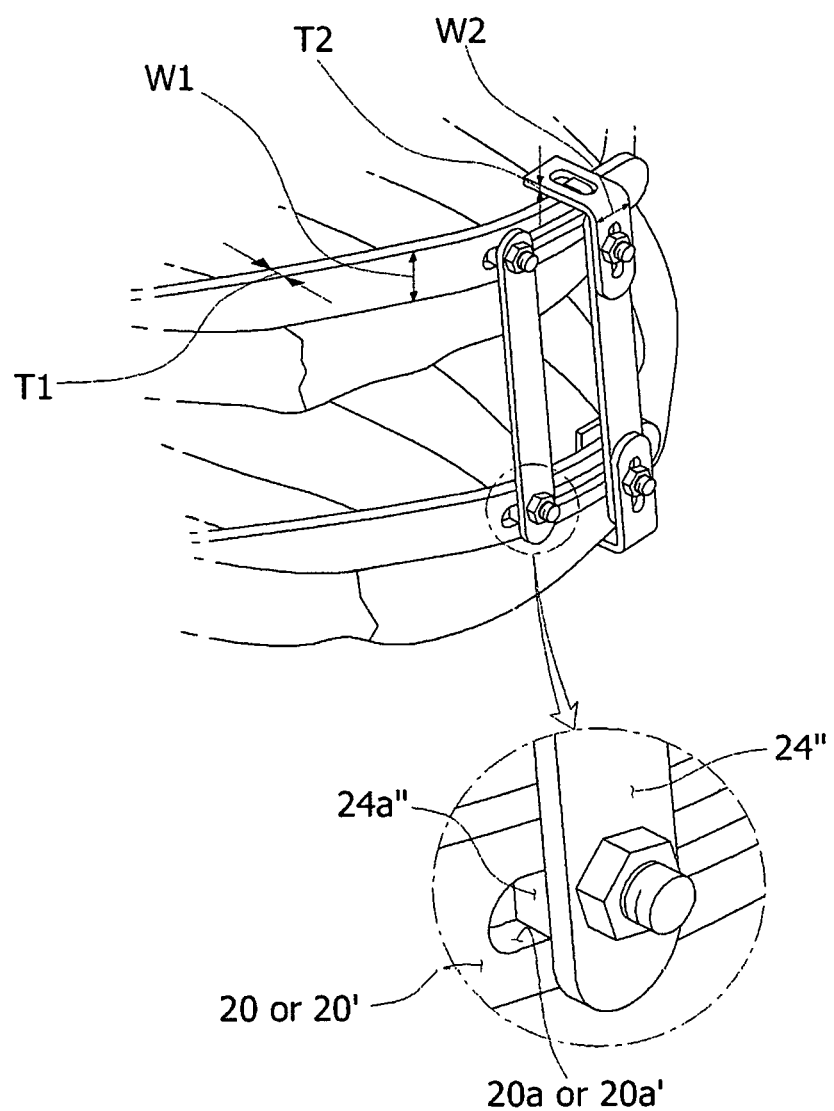
FIG. 4 is a magnified perspective view for describing how pectus bars, brackets, and bridges of FIG. 3 are coupled using coupling units.
Figure 5:
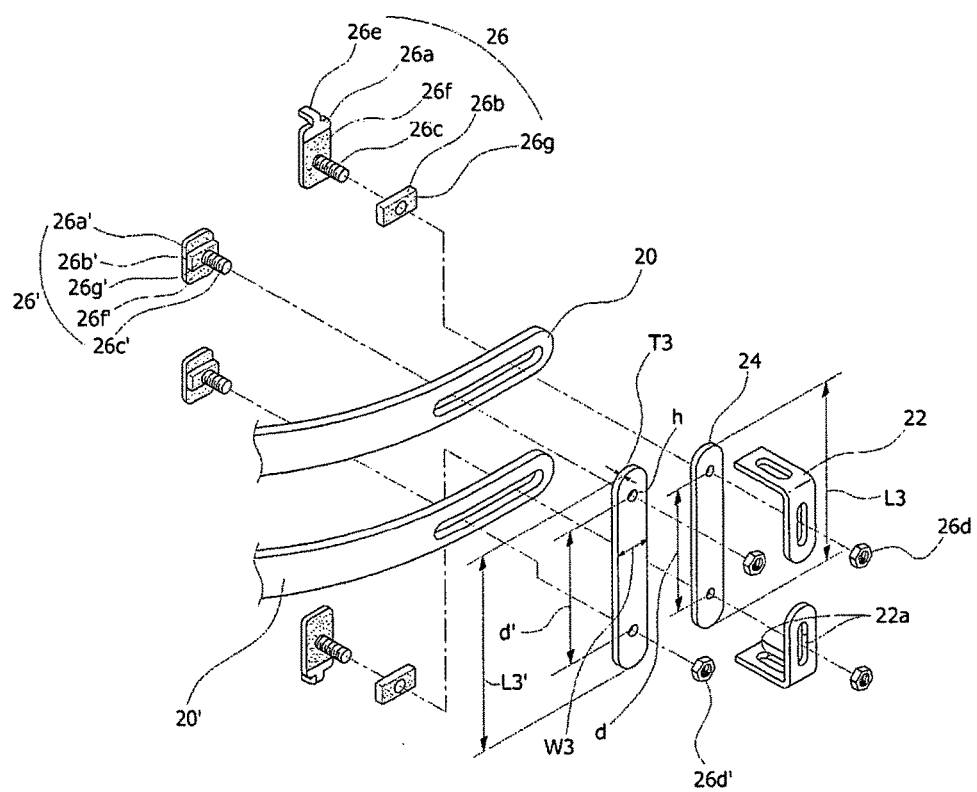
FIG. 5 is an exploded perspective view of the coupling units.

Although the second long hole 22a is provided in each of the first and second sides of the bent part of the bracket 22 in FIGS. 3 to 5, the second long hole 22a may extend from the second side through the bent part to the first side of the bracket 22, or may be provided in only the second side of the bent part.

The second long hole 22a of the bracket 22 may be provided in the second side of the bent part of the bracket 22 along the length direction of the bracket 22 to facilitate coupling between a bolt B and a nut N of a coupling units 26 and 26'. A description thereof will be given below.

Alternatively, the second long hole 22a of the bracket 22 may extend from the second side through the bent part to the first side or may be provided in each of the first and second sides not only to facilitate coupling between the bolt B and the nut N of the coupling units 26 and 26' but also to prevent displacement of the pectus bar 20 or 20' by inserting a plug 26b extended from a supporting part 26a, into the second long hole 22a. A description thereof will be given below.

Among the above-described elements of the present invention, the bridges 24 and 24' have plate shapes having a width W3, a thickness T3, and lengths L3 and L3'. When the two pectus bars 20 and 20' are provided at upper and lower sites of the chest of the patient, the bridges 24 and 24' are provided to cross the pectus bars 20 and 20' not only to partially fix the pectus bars 20 and 20' due to coupling of bolts B and nuts N of coupling units 26 and 26' but also to maintain distances d and d' between the upper and lower pectus bars 20 and 20'.

To this end, the bridges 24 and 24' have the lengths L3 and L3' corresponding to the vertical distances d and d' between the pectus bars 20 and 20', which are set for the patient. Through-holes h corresponding to the bolts B of the coupling units 26 and 26' are provided in two length-direction ends of the bridges 24 and 24' and are spaced apart from each other by the vertical distances d and d' between the pectus bars 20 and 20'.

Herein, the above-described distance d or d' between the through-holes h in the bridge 24 or 24' differs between neighboring bridges 24 and 24'.

A set of the bridges 24 and 24' includes a first bridge 24 for maintaining a certain distance between the upper and lower pectus bars 20 and 20' by using the above-described brackets 22, and a second bridge 24' for configuring a set together with the first bridge 24, having a length different from that of the first bridge 24, and provided in parallel to the first bridge 24.

The through-holes h in the two length-direction (L3') ends of the second bridge 24' are aligned to cross the first long holes 20a and 20a' in the upper and lower pectus bars 20 and 20', and the second bridge 24' is fixed using the coupling units 26 and 26'.

That is, the second bridge 24' may not use the brackets 22, and is fixed to the pectus bars 20 and 20' through the first long holes 20a and 20a' using the coupling units 26', thereby maintaining the distance between the pectus bars 20 and 20' in addition to the first bridge 24.

Herein, when the second bridge 24' is installed at a front side of the first bridge 24, the length L3' thereof and the distance d' between the through-holes h in the two ends thereof may be greater or less that the length L3 of the neighboring first bridge 24 and the distance d between the through-holes h in the two ends thereof, by a preset rate.

On the other hand, when the second bridge 24' is installed at a rear side of the first bridge 24, the length L3' of the second bridge 24' and the distance d' between the through-holes h in the two ends thereof may be less or greater than the length L3 of the neighboring first bridge 24 and the distance d between the through-holes h in the two ends thereof, by a preset rate.

As such, the distance between the upper and lower pectus bars 20 and 20' at central parts thereof may be greater or less than the distance d therebetween set by the through-holes h of the first bridge 24, and thus the central parts of the two pectus bars 20 and 20' may be far away from or close to each other compared to the two fixed ends thereof.

Since the upper and lower pectus bars 20 and 20' are provided to form a certain angle θ therebetween as described above, the restoring forces of the sternum 12 and the rib cartilages 14, which tend to return to original shapes thereof before correction, push the central part of the upper pectus bar 20 in an upward direction indicated by an arrow C, and push the central part of the lower pectus bar 20' in a downward direction indicated by an arrow C', as illustrated in FIG. 3.

In this case, since the second bridge 24' maintains the distances d and d' between the upper and lower pectus bars 20 and 20', displacement of the upper and lower pectus bars 20 and 20' in opposite directions due to the restoring forces of the sternum 12 and the rib cartilages 14 may be complementarily prevented.

That is, the upper pectus bar 20 is provided at a location to be pushed upward due to the restoring forces of the sternum 12 and the rib cartilages 14, the lower pectus bar 20' is provided at a location to be pushed downward, and the upper and lower pectus bars 20 and 20' are fixed by the first and second bridges 24 and 24' to form a certain angle therebetween, thereby complementarily preventing displacement thereof.

Differently from the above description of the second bridge 24', the length of the second bridge 24' provided at a front side of the first bridge 24 may be less than that of the first bridge 24, or the length of the second bridge 24' provided at a rear side of the first bridge 24 may be greater than that of the first bridge 24.

As such, the distance between the upper and lower pectus bars 20 and 20' at central parts thereof may be set to be less than the distance d between the fixed two ends thereof in consideration of directions of the restoring forces of the sternum 12 and the rib cartilages or possibilities of damage to organs inside the rib cage.

Accordingly, the lengths and positions of the first and second bridges 24 and 24' are selectively determined based on pectus excavatum of the patient.

According to another embodiment, like the above-described first bridge 24, a third bridge 24" illustrated in FIG. 4 is provided to interconnect the two ends of the upper and lower pectus bars 20 and 20', and projections 24a" to be inserted into the first long holes 20a and 20a' of the pectus bars 20 and 20' are provided to extend from sides of one or more of the through-holes h in two length-direction (L3") ends of the third bridge 24".

When the coupling units 26' are fixed through the through-holes h, the projections 24a" are supported by inner walls of the first long holes 20a and 20a'. As such, the pectus bars 20 and 20' may move forward and backward along the first long holes 20a and 20a' and, at the same time, displacement of the central parts of the pectus bars 20 and 20' may be prevented.

That is, the first long holes 20a and 20a' are supported by the coupling unit 26 or 26' and the projections 24a" through the through-holes h as illustrated in FIG. 4, the upper and lower pectus bars 20 and 20' interconnected by the third bridge 24" may be guided in forward and backward directions and may maintain an angle therebetween.

As illustrated in FIG. 5, the coupling units 26 and 26' of the present invention include supporting parts 26a and 26a' provided between the ribs 10 and the pectus bars 20 and 20', slide 26b protruding from outer surfaces of the supporting parts 26a and 26a' to be slidable along the first long holes 20a and 20a', first coupling part 26c provided at central parts of the slide 26b, and second coupling part 26d for fixing the brackets 22 and the bridges 24, 24', and 24" provided on coupling paths between the first coupling part 26c through overlapping parts of the first and second long holes 20a, 20a', and 22a and the through-holes h of the bridges 24, 24', and 24".

Herein, the height of the above-described slide 26b protruding from the outer surfaces of the supporting parts 26a and 26a' is greater than the thickness of the pectus bars 20 and 20', the brackets 22 and the bridges 24, 24' and 24" are fixed to each other by receiving support of outer surfaces of the slides 26b and coupling the first coupling parts 26c to the second coupling parts 26d, and the pectus bars 20 and 20' are guided by the slide 26b to be slidable along length directions of the first long holes 20a and 20a'.

The above-described supporting parts 26a and 26a' may include plugs 26e extending and protruding therefrom to cross the pectus bars 20 and 20' in a plate shape and inserted into the second long holes 22a.

The first coupling part 26c may include bolts integrally protruding from the outer surfaces of the supporting parts 26a and 26a', and first rough surface 26f may be provided around the bolts on the outer surfaces of the supporting parts 26a and 26a'.

Holes through which the bolts pass may be provided in the slide 26b, and second rough surfaces 26g and 26g' corresponding to the first rough surfaces 26f and 26f' may be provided around the holes on inner and outer surfaces of the slide 26b.

As described above, since the integrally provided bolts are coupled to the nuts through the first and second long holes 20a, 20a', and 22a, which cross each other, and the through-holes h of the bridge 24 and the plugs 26e of the supporting parts 26a are inserted into the second long holes 22a, the supporting parts 26a are supported by the brackets 22 and thus displacement thereof is prevented.

The brackets 22 are supported by the ribs 10 and thus displacement thereof is prevented.

Since the second rough surface 26g is pressed to contact the first rough surface 26f due to coupling of the bolts and the nuts of the coupling units 26 and 26', displacement of the slide 26b is prevented.

As such, the pectus bars 20 and 20' are supported by the slide 26b and thus displacement thereof is prevented.

As described above, even when deformity of the sternum 12 and the rib cartilages 14 is correctable using one pectus bar 20 or 20', the supporting parts 26a and 26a' having the plugs 26e and the first rough surface 26f, the slide 26b having the second rough surface 26g corresponding to the first rough surface 26f, and the coupling units 26 and 26' having a bolt-nut coupling structure may also prevent displacement of the pectus bar 20 or 20'.

That is, a pectus excavatum correction apparatus according to a modified example of the present invention may prevent displacement of the pectus bar 20 or 20' without using the above-described bridges 24, 24', and 24".

The invention claimed is:

1. A pectus excavatum correction apparatus comprising:
   two pectus bars each made of a stick plate having a width, thickness, length, curved shape, rigidity, and elastic restoring force designed to correspond to a predetermined treatment site of a patient, each comprising first long holes in length-direction ends of each of the two pectus bars, and spaced apart from each other in a vertical direction of the patient with respect to the length-direction of the pectus bar;
   brackets each having a plate shape having a length-direction bent part, wherein a first side of the bent part is configured to be hooked onto an upper or lower part of a rib, a second side of the bent part crosses and faces an outer surface of the pectus bar, and a second long hole is provided in at least the second side of the bent part along the length direction of the bracket;
   a first bridge having through-holes provided in two length-direction ends of the first bridge and spaced apart from each other by a preset first distance to correspond to end-direction positions of the pectus bars within the upper and lower first long holes;
   a second bridge forming a pair of bridges together with the first bridge and having through-holes provided in two length-direction ends of the second bridge and spaced apart from each other by a preset second distance to correspond to center-direction positions of the pectus bars within the upper and lower first long holes; and
   coupling units each comprising a supporting part provided between the rib and the pectus bar, a slide protruding from an outer surface of the supporting part and inserted to be slidable along the first long hole, a first coupling part provided at a center of an outer surface of the slide, and a second coupling part coupled to the first coupling part to press and fix the pectus bar, the bracket, and the bridge provided on a coupling path between the first and second coupling parts through an overlapping part of the first and second long holes and the through-hole,
   wherein the second distance is greater or less than the first distance within a preset range.

2. The pectus excavatum correction apparatus of claim 1, wherein the second bridge is fixed using the coupling units without using the brackets to correspond to the first long holes of the pectus bars.

3. The pectus excavatum correction apparatus of claim 1, wherein a height of the slide protruding from the outer surface of the supporting part is greater than the thickness of the pectus bar,
   wherein the bracket and the bridge are fixed to each other by receiving support of the outer surface of the slide and coupling the first coupling part to the second coupling part, and
   wherein the pectus bar is guided by the slide to be slidable along a length direction of the first long hole.

4. The pectus excavatum correction apparatus of claim 3, wherein the first coupling part comprises a bolt integrally protruding from the outer surface of the supporting part,
   wherein the supporting part comprises a plug extending and protruding therefrom to cross the pectus bar and to be inserted into the second long hole, and a first rough surface provided around the first coupling part on the outer surface of the supporting part, and
   wherein the slide comprises a hole for penetrating the bolt therethrough, and second rough surfaces provided around the hole on inner and outer surfaces of the slide to correspond to the first rough surface.

5. A pectus excavatum correction apparatus comprising:
   pectus bars each having a width, thickness, length, curved shape, rigidity, and elastic restoring force designed to correspond to a predetermined treatment site of a patient, and each comprising first long holes in length-direction ends of each of the pectus bars along a center line of the width;
   brackets each having a plate shape having a length-direction bent part, wherein a first side of the bent part is configured to be hooked onto an upper or lower part of a rib, a second side of the bent part crosses and faces an outer surface of the pectus bar, and a second long hole is provided in at least the second side of the bent part along the length direction of the bracket; and
   coupling units each comprising a supporting part having a plate shape provided between the rib and the pectus bar and comprising a bolt integrally protruding from a center of an outer surface of the supporting part, a plug extending therefrom to be inserted into the second long hole, and a first rough surface provided around the bolt on the outer surface of the supporting part, a slide inserted to be slidable along the first long hole and comprising a hole for penetrating the bolt therethrough, and second rough surfaces provided around the hole on inner and outer surfaces of the slide to correspond to the first rough surface, and a nut coupled to the bolt protruding through an overlapping part of the first and second long holes and the through-hole to press and fix the bracket provided between the bolt and the nut.

* * * * *